United States Patent [19]

Graetz

[11] 4,031,897

[45] June 28, 1977

[54] COLLECTOR FOR AMNIOTIC FLUID

[76] Inventor: Adan Graetz, Apartado Postal 374, Cuernavaca, Mor, Mexico

[22] Filed: Apr. 21, 1976

[21] Appl. No.: 679,060

[52] U.S. Cl. .............................................. 128/286
[51] Int. Cl.² .......................................... A61F 5/44
[58] Field of Search .......... 128/283, 284, 286, 287, 128/290 R, 292, 296; 119/95; 4/121, 142

[56] References Cited

UNITED STATES PATENTS

| 514,717 | 2/1894 | Kirwin | 128/286 |
|---|---|---|---|
| 1,494,060 | 5/1924 | Camp | 128/286 |
| 2,713,341 | 7/1955 | Chambers | 128/286 |
| 3,577,989 | 5/1971 | Anderson | 128/283 |
| 3,804,093 | 4/1974 | Fell | 128/286 |

Primary Examiner—Robert W. Michell
Assistant Examiner—Henry S. Layton
Attorney, Agent, or Firm—Mandeville and Schweitzer

[57] ABSTRACT

The disclosure relates to an article, suitable to be worn unobtrusively and with comfort by a woman in the last stages of pregnancy, which is positioned to receive and retain the amniotic fluids when released. The article may conveniently be in a form similar to a sanitary napkin belt, or may be constructed into a hospital garment, for example. Although the fluid receptacle is capable of containing a substantial volume of amniotic fluid (as much as three liters), the article of the invention provides for the receptacle to be retained in a convenient and unobtrusive compressed condition until such time as the need arises for collection of the fluid.

13 Claims, 8 Drawing Figures

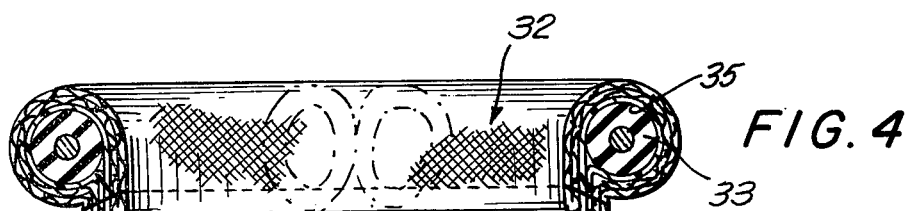
U.S. Patent   June 28, 1977   Sheet 2 of 2   4,031,897
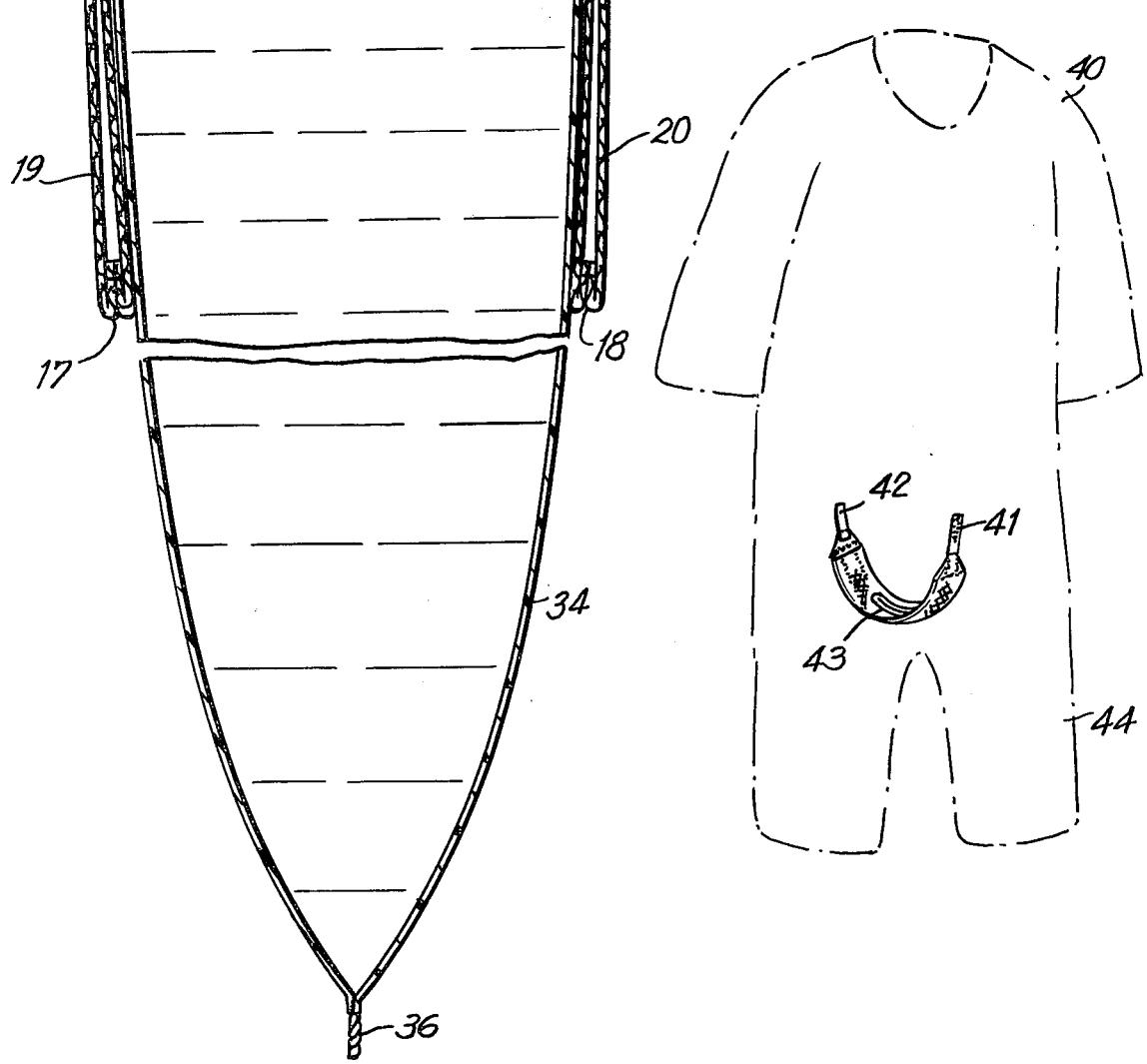
FIG. 4
FIG. 5

COLLECTOR FOR AMNIOTIC FLUID

BACKGROUND AND SUMMARY OF THE INVENTION

I have established by my prior work that the amniotic fluid, which surrounds the fetus and is released by the mother prior to child birth, is possessed of significant and potentially valuable therepeutic properties and thus constitutes a valuable therapeutic resource. Among other things, the amniotic fluid has been found to contain certain isoantigens which have been experimentally established to have important therapeutic value. A pregnant woman typically will hold as much as a liter or more of amniotic fluid, and the collection, preservation and processing of such fluid can have substantial medical value. Unfortunately, amniotic fluid is released by the prospective mother shortly before child birth, typically without much advance warning and frequently during the night while the expectant mother is asleep. Accordingly, as a general rule, this valuable liquid is lost.

In accordance with the invention, a simple and convenient article of apparel is provided, which may be worn at all times by the expectant mother with comfort and convenience and which is capable of effectively collecting and retaining for subsequent use the amniotic fluid, when released. The article of the invention includes a fluid receptacle of relatively large volumetric capacity (e.g. up to 3 liters) which nevertheless may be worn unobtrusively. To this end, the receptacle is in the form of a flexible plastic bag, which is normally retained, by a pocket or other facility in the garment, in collapsed and folded condition, occupying a minimum of space. For ambulatory use, the collection receptacle is maintained in its folded and compressed condition, but is capable of being instantly opened made ready for the reception of fluid, in the event of the sudden onset of fluid release. For nighttime wear, the receptacle may be extended upon retiring so as to be able to collect amniotic fluid if released during sleep.

Desirably, the fluid collector device of the invention includes a non-elastically conformable reinforcement secured to and surrounding the opening of the receptacle. This reinforcement may be shaped by the wearer for maximum comfort, consistent with maintaining a proper opening at the top of the receptacle. Upon discharge of amniotic fluid into the receptacle, the conformable reinforcement may be pressed closed, to facilitate retention of the fluid until its delivery to a processing center.

PRIOR ART OF INTEREST

Representative of prior art known to the applicant are the following U.S. Patents: Schilling U.S. Pat. No. 205,912, Kirwin U.S. Pat. No. 514,717, Shtuchka U.S. Pat. No. 844,198 and Kargul U.S. Pat. No. 3,230,956. The first three recited patents relate to varieties of catamential receptacles. However, none of them envisions the volumetric requirements of a device for the collection of amniotic fluid, and none provides for the collection receptacle to be pre-folded into a compact, unobtrusive form for normal, ambulatory use. The Kargul patent illustrates a form of a pre-foled container attached to a sanitary napkin. However, the container is neither intended for nor used as a receptacle for fluids, but is merely a facility for enclosing and disposing of the used napkin.

For a more complete understanding of the above mentioned and other features and advantages of the invention, reference should be made to the following detailed description of preferred embodiments and to the accompanying drawing.

DESCRIPTION OF THE DRAWING

FIG. 4 is an enlarged cross sectional view, similar to FIG. 3, but with the receptacle fully extended for the reception of fluid.

FIG. 5 is a simplified, perspective view illustrating the manner in which the article of the invention may be incorporated in a hospital garment, for example.

DESCRIPTION OF PREFERRED EMBODIMENTS

Figure 2:
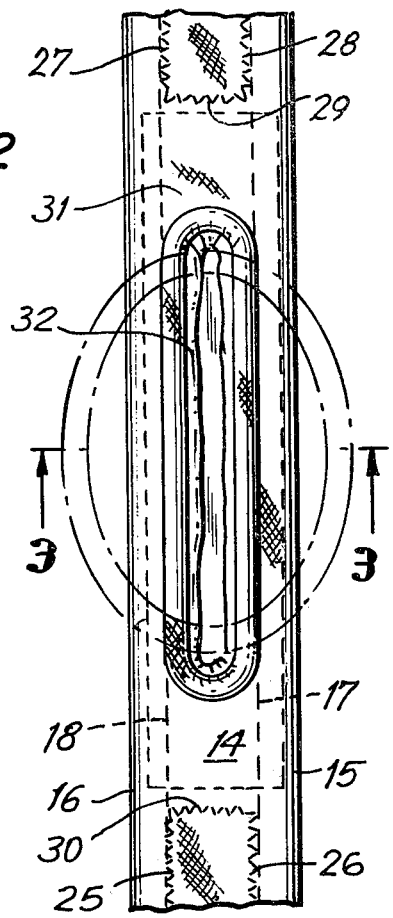
FIG. 2 is a fragmentary plan view of the article of FIG. 1.
Figure 1:
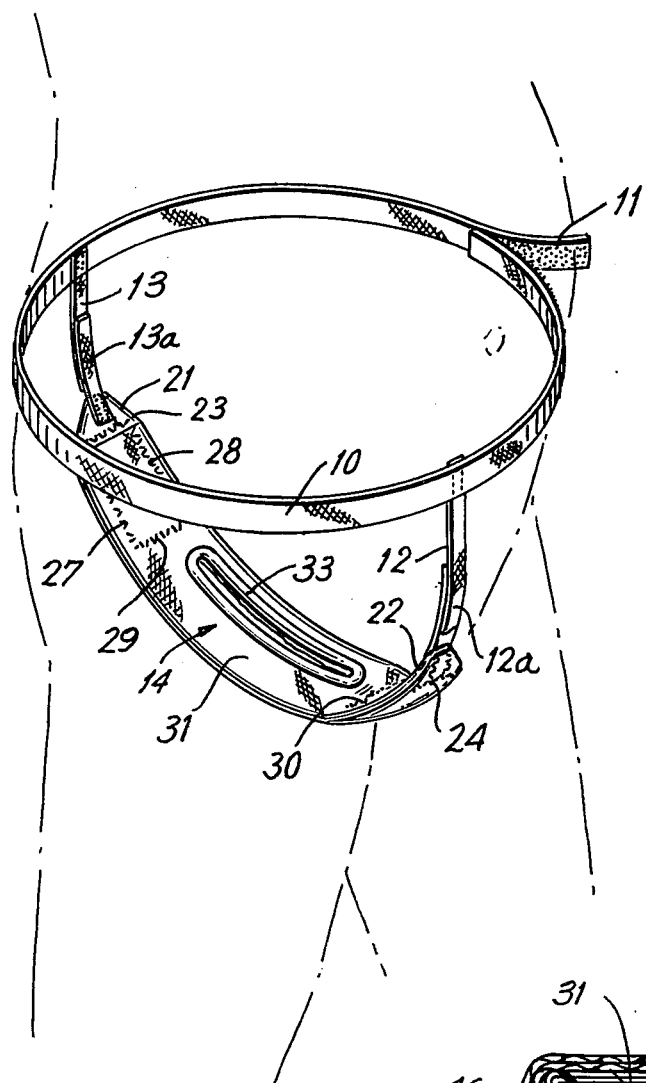
FIG. 1 is a perspective view of the device of the invention as shown in condition for normal ambulatory use.

Refering now to the drawing, and initially to FIGS. 1–4 thereof, one advantageous form of the invention is constructed in a manner similar to a conventional belt support for sanitary napkins. Thus, a waste-encircling belt 10 is provided, which, in this instance is provided with a substantial length adjustment capability, in order to accommodate the pregnant condition of the expectant mother. To advantage, in this respect, the belt 10 may incorporate one or more sections 11 of hook and loop fastening tape, such as is available under the trademark Velcro.

Secured to and extending downwardly from the belt 10 are front and back supporting straps 12, 13. These supporting straps, which may also incorporate Velcro adjustment portions 12a, 13a are secured to each end of a receptacle-retaining envelope 14. Typically and advantageously, the envelope 14 may have length and width dimensions not unlike those of a conventional sanitary napkin, for example. The envelope 14 may be constructed of a lightweight, limp, open mesh fabric, edge margins of which are foled under along longitudinal side edges 15, 16. The circumference dimension of the fabric section is somewhat greater than twice the overall width of the envelope 14 such that, in the folded condition, one fabric edge 17 overlaps and extends beyond the other edge 18 by a substantial amount. By way of example only, in a practical embodiment in which the envelope has a width on the order of 75 mm, the construction may be such as to provide for folded-under flap-like fabric margins of around 60 mm, so that an outer flap 19 overlaps the under flap 20 by, say, around 50 mm.

At the ends, the envelope 14 desirably is folded to form tapered ends 21, 22, and these may be seamed across at 23, 24 to close the ends of the envelope. In addition, the respective fabric edges 17, 18 desirably are stitched at 25–28, for a short distance from the end seams 23, 24 toward the center of the envelope. Significantly, the longitudinal seams 25–28 extend only a portion of the length of the envelope between the end seams. In the illustrated, typical embodiment, having a representative overall length between the end seams 23, 24 of around 350 mm, the longitudinal seams 25–28 may extend for a distance of, say, 70 or 75 mm, being connected at their inner ends by short rows of cross stitching 29, 30. Between the inner rows of cross stitching 29, 30, the overlapping margins 19, 20 are left free, forming an internal pocket 31 in the envelope which is accessible by displacement of the outer fabric section 19 in one direction and similar displacement in the opposite direction of the inner fabric layer 20. Although specific dimensions are not in any sense critical to the invention, the length of the envelope pocket, formed between the rows of cross stitching 29, 30, may typically be on the order of 170–180 mm. The closed portions of the envelope 14, extending beyond the pocket at each end, serve to primarily provide a convenient and comfortable support for the pocket section.

Figure 3:
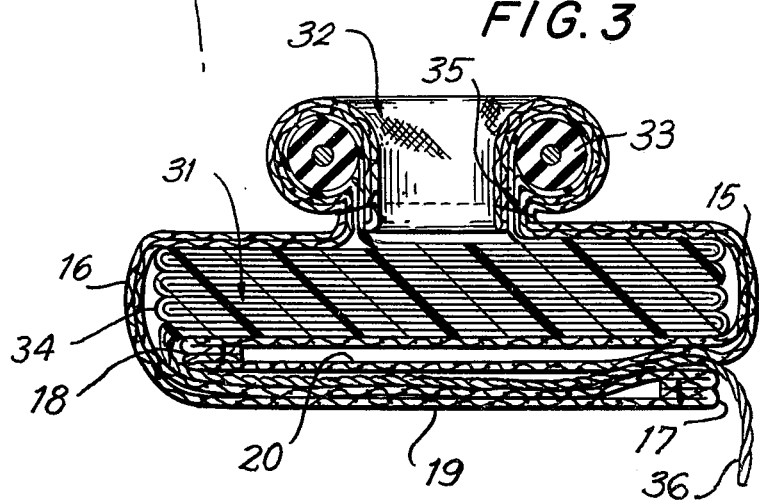
FIG. 3 is an enlarged cross sectional view as taken generally on line 3—3 of FIG. 2, showing the article with the receptacle in a foled, compressed condition suitable for ambulatory use.

On the upper side of the pocket 31, there is formed a relatively large opening 32 which, in normal use may be of generally oval shape, having typical major and minor dimensions of around 130 mm and around 60 mm respectively, it being again understood that specific dimension are not critical to the invention. Around the opening 32 there is provided a reinforcing member 33, of generally endless configuration, which is of a yieldable, conformable material, substantially non-elastic in nature. The arrangement is such that the reinforcement may be shaped three-dimensionally by the expectant mother to conform most comfortably to her body contours. As illustrated in FIG. 3, the reinforcing member 33 is completely enveloped by the fabric material and is secured to the edges of the pocket opening 32, such that, in general, the reinforcing member 33 defines the size and the shape of the pocket opening.

Securely attached to the upper layer of the pocket forming fabric, and also to the reinforcing member 33, is a relativey large bag-like receptacle 34, which is formed of a lightweight, strong, highly flexible plastic material. Desirably, the width of the bag-like receptacle (measured in the longitudinal direction of the envelope 14) is approximately equal to the length of the pocket 31. The receptacle is of substantial vertical length, sufficient to provide for a maxiumum volumetric capacity of as much as three liters, although that is typically considerably in excess of the amount of amniotic fluid to be received.

In accordance with the invention, the open upper end 35 of the bag-like receptacle 34 is secured about is periphery to the reinforcing member 33, or at least to the fabric in the area of the reinforcing member. When fully extended, the receptacle 34 extends through the open pocket bottom formed by the displaced fabric flaps 19, 20 (see FIG. 4).

In accordance with a significant aspect of the invention, the flexible, bag-like receptacle 34 may be folded acordion fashion, forming four or five flat layers of material, and tucked inside the pocket 31, with the pocket-closing flaps 19, 20 being closed over the receptacle, serving to effectively retain the accordion folded receptacle in a flat, unobtrusive condition inside the pocket 31. This enables the article to be worn by the expectant mother with convenience and comfort and in an entirely unobtrusive manner. The overall dimensions of the envelope 14, containing the accordion folder receptacle are not unlike those of a conventional sanitary napkin, for example.

Since experience indicates that the onset of discharge of the amniotic fluid may proceed with very little advance warning, provision is made for effecting instant release of the folded receptacle from its pocket 31, to bring the receptacle into its fully extended condition ready to receive the fluid. To this end, the bottom of the bag is provided wih a tab or cord 36, which is permitted to extend through the normally overlapped pocket-closing flaps 19, 20, and is capable of being easily and quickly grasped. Thus, when the expectant mother detects the onset of fluid release, she need only pull the tab or cord 36 and draw the bag downwardly out of the pocket to receive the fluid discharge.

Frequently, the onset of amniotic fluid discharge occurs without warning, while the mother is asleep at night. Accordingly, it is generally desirable for the expectant mother to draw the receptacle 34 out to its fluid-receiving condition before retiring at night. The next morning, the article may be prepared for ambulatory use by simply refolding the receptacle and tucking it back into the pocket 31.

As mentioned above, the non-resiliently comformable reinforcing members 33 may be shaped by the user to a comfortable, body-conforming contour for normal use. In addition, after amniotic fluid has been discharge into the receptacle bag 34, and the bag has been removed from the body of the user, the opening 32 may conveniently be closed by squeezing tightly together opposite sides of the conformable reinforcing member (see phantom line illustration, FIG. 4). While not providing an absolute seal, this can largely prevent accidental loss of fluid by free surface action as well as contamination of the fluid by entry into the receptacle of foreign matter. It further enables the filled receptacle to be conveniently carried to another location where the fluid can be processed in a suitable fashion and stored for subsequent use.

The form of the invention shown in FIG. 5 may be advantageous for institutional use, as well as for use at night. The modification of FIG. 5 includes a suitable loose fitting garment 40, which may advantageously be of a one-piece design. The garment 40 is fitted with Velcro or similar fasteners for the adjustable engagement of front and back envelope-supporting straps 41, 42, engaging the opposite ends of a receptacle containing envelope 43. The envelope structure 43 is in all respects the same as that described with reference to FIGS. 1–4, it being understood, however, that the envelope 43 is supported directly by the garment 40, rather than by a separate belt structure. When ready for use, the receptacle may be drawn out to extend into one of the loosefitting, abbreviated by portions 44 of the garment.

In any of its various forms, the article of the invention provides a comfortable and convenient, yet entirely practical arrangement for the collection of valuable amniotic fluids when discharged from an expectant mother. The article of the invention accommodates the circumstance, that the onset of fluid discharge occurs with little or no advance warning, thus rendering it impractical for an expectant mother to wear a catamenial device of conventional construction having adequate volumetric capacity to receive the amniotic fluid discharge. With the article of the present invention, the fluid-receiving receptacle is accordion folded into flat, compact, body-conforming configuration of a size and shape to which the average female is already accustomed. On a moment's notice, however, this may be converted into a usable receptacle of substantial volumetric capacity.

With the article of the invention, the heretofore wasted, but nevertheless therapeutically valuable and important amniotic fluid may be collected and utilized in a practical manner, affording significant benefits not only to the mother and infant, but in many cases also to third parties. Thus, while the device itself is relatively simple and inexpensive in nature, its practical advantages and benefits are far-reaching and medically significant.

It should be understood, of course, that the specific form of the invention herein illustrated and described are intended to be representative only, as certain changes may be made therein without departing from the clear teachings of the disclosure. Accordingly, reference should be made to the following appended claims in determining the full scope of the invention.

I claim:

1. An article for collecting and retaining amniotic fluid discharged from an expectant mother, which comprises
   a. body encircling support means,
   b. a flat, flexible pocket-forming member engaged at forward and rearward ends by said support means,
   c. said pocket-forming member having a fluid receiving opening in its upper portion,
   d. a fluid receiving receptacle formed of lightweight, flexible, foldable material and having its open upper end secured to and communicating with said openings,
   e. a flat pocket formed in said pocket-forming member, below said fluid receiving opening, for the reception and containment of said receptacle in a flat, folded condition,
   f. said receptacle being quickly removable from said pocket while said article is being worn by the user, to place said receptacle in fluid receiving condition.

2. An article according to claim 1, further characterized by
   a. said body encircling support being in the form of a belt.

3. An article according to claim 1, further characterized by
   a. said body encircling support being in the form of a loose fitting, body covering garment.

4. An article according to claim 1, further characterized by
   a. a non-elastically conformable reinforcing member surrounding and defining said fluid receiving opening.

5. An article according to claim 1, further characterized by
   a. said pocket-forming member comprising a member of lightweight, limp open mesh fabric having under folded flap-forming margins arranged one overlapping the other,
   said flap-forming margins being secured near their ends but free over a length corresponding to the width of said receptacle,
   c. said flap-forming margins serving to form a normally closed, central-opening, flap pocket for the reception of said receptacle in flat, accordion-folded condition.

6. An article according to claim 5, further characterized by
   a. said receptacle having a tab-like appendage at its lower end engageable from outside of said pocket when said receptacle is received therein.

7. A device for collecting and retaining amniotic fluid, which comprises
   a. an elongated piece of limp material adapted to cover the external reproductive organs of a female wearer and including an externally accessible internal pocket,
   said piece of material provided with a fluid-receiving opening, and
   c. a flexible bag-like receptacle having a folded form andbeing normally disposed within said internal pocket and including an open top portion communicating with said fluid-receiving opening,
   said bag-like receptacle being unfoldable and extensible out of said pocket whereby a discharge of amniotic fluid through the opening may be received into said bag.

8. The device of claim 7, further characterized by
   a. said piece of material comprising a section of open mesh fabric folded lengthwise along edge portions thereof to form overlapping folds thereby providing said internal pocket, and
   b. said overlapping folds being fastened to one another at spaced regions adjacent the ends of said section of fabric whereby said internal pocket is accessible from the exterior of said section of fabric through the unfastened portion of said overlapping folds.

9. The device of claim 8, further characterized by
   a. said fluid-receiving opening provided with a ring-like element secured to the periphery thereof and being made from a non-elastic, deformable material whereby the bag may be closed after discharge of the amniotic fluid.

10. The device of claim 7, further characterized by
    a. said bag comprising a plastic bag.

11. The device of claim 7, further characterized by
    a. said piece of material being provided at the ends thereof with support straps, and
    b. a waistband connected to said support straps and adapted to be worn by said female wearer whereby said piece of material is supported against the external reproductive organs.

12. The device of claim 7, further characterized by
    a. said piece of material being secured in the crotch area of a body covering garment.

13. The device of claim 12, further characterized by
    a. said garment being loose fitting at said crotch to accommodate the bag in its unfolded form.

* * * * *